(12) United States Patent
Lin

(10) Patent No.: US 11,174,653 B2
(45) Date of Patent: Nov. 16, 2021

(54) PRODUCTION AND CONSUMPTION SYSTEM OF THREE-DIMENSIONAL VERTICAL PLANTING LANDSCAPE AND CAPABLE OF ACHIEVING HEALTHY, LOW-COST AND ENVIRONMENTAL PROTECTION

(71) Applicant: James C. Lin, Tainan (TW)

(72) Inventor: James C. Lin, Tainan (TW)

( * ) Notice: Subject to any disclaimer, the term of this patent is extended or adjusted under 35 U.S.C. 154(b) by 473 days.

(21) Appl. No.: 16/274,431

(22) Filed: Feb. 13, 2019

(65) Prior Publication Data

US 2020/0256077 A1 Aug. 13, 2020

(51) Int. Cl.
| | | |
|---|---|---|
| *G06Q 30/00* | (2012.01) | |
| *E04H 5/08* | (2006.01) | |
| *G06Q 30/06* | (2012.01) | |
| *G06Q 50/02* | (2012.01) | |
| *E04H 6/00* | (2006.01) | |

(52) U.S. Cl.
CPC ............. *E04H 5/08* (2013.01); *E04H 6/00* (2013.01); *G06Q 30/0631* (2013.01); *G06Q 50/02* (2013.01)

(58) Field of Classification Search
None
See application file for complete search history.

(56) References Cited

U.S. PATENT DOCUMENTS

| | | | | |
|---|---|---|---|---|
| 2015/0101539 A1* | 4/2015 | Northrop | ............... | A01K 63/04 119/226 |
| 2015/0250812 A1* | 9/2015 | Bartel | ................. | A61K 31/198 514/52 |
| 2018/0016804 A1* | 1/2018 | Irons | ........................ | A01G 9/14 |
| 2018/0036591 A1* | 2/2018 | King | ........................ | G09B 5/02 |

FOREIGN PATENT DOCUMENTS

| | | |
|---|---|---|
| TW | 201204242 A | 2/2012 |
| TW | M527997 U | 9/2016 |
| TW | M543545 U | 6/2017 |
| TW | M547138 U | 8/2017 |

OTHER PUBLICATIONS

STIC EIC 3600 Search Report for U.S. Appl. No. 16/274,431 dated Jul. 15, 2021 (Year: 2021).*
IP.com search strategy dated Jul. 23, 2021 (Year: 2021).*

* cited by examiner

*Primary Examiner* — Matthew T Sittner

(74) *Attorney, Agent, or Firm* — Rosenberg, Klein & Lee

(57) ABSTRACT

A production and consumption system of three-dimensional vertical planting landscape and capable of achieving healthy, low-cost and environmental protection includes an aquatic raising zone, a crop planting zone, an animal raising zone, an insect culturing zone, a food processing zone, a consumption zone, a sport health zone, providing a shopping suggestion list automatically for reference based on a consumer's purchase traceability, and offering a sport suggestion list and a food suggestion list that are suitable for the consumer based on a physiological data so as to allow the consumer to do exercise and control diet, thereby attaining effects of low-cost, environmental protection, super-freshness, high efficiency, high quality of production of vegetables, meat and aquatic products, and functions of purchase, health, shopping, tourism, exercise, fitness and health monitoring.

20 Claims, 6 Drawing Sheets

PRODUCTION AND CONSUMPTION SYSTEM OF THREE-DIMENSIONAL VERTICAL PLANTING LANDSCAPE AND CAPABLE OF ACHIEVING HEALTHY, LOW-COST AND ENVIRONMENTAL PROTECTION

BACKGROUND OF THE INVENTION

1. Field of the Invention

This invention relates to a production and consumption system combining consumption, exercise and health and integrating various industries of agriculture, fishery and animal husbandry to provide a shopping suggestion list, a sport suggestion list and a food suggestion list automatically to allow a consumer to do exercise and control diet.

2. Description of the Related Art

Vegetables, aquatic and meat products produced by agriculture, fishery and animal husbandry are the main food sources of human beings currently. However, owing to food shortage or drastic changes in prices of food, and a large amount of somatorophic hormone, antibiotics and pesticides is used in a growing process of vegetables and meat, it causes crises of food safety, livelihood and economy. Moreover, the planting and raising operations of the above-mentioned agriculture, fishery and animal husbandry require a large space for accommodation and a large amount of manpower and material resources. In addition, costs for transportation, inspection, freshness retaining and storage of meat, aquatic products and vegetables increase continuously. Therefore, it becomes an important issue how to create the largest amount of food supply and consumption with a limited resource when the source shortage becomes increasingly serious that has yet to be studied and overcame by countries. Nowadays, it takes a long time to produce, process, transport and store food. When the food reaches a consumer, it has already taken a long time and that increases related expenses. Further, the freshness of the food is not enough and the consumer cannot taste the freshest food.

Therefore, the Taiwan Patent Publication No. 201204242 "duckery method combining with ecocycling and apparatus thereof" published on Feb. 1, 101st year of the Republic Era takes an advantage of a hydrotropic property of ducks and cooperates with a floating rearing device which rears a limited area of water face of the whole water area. Water quality and pest treatment of germ are used to make the feces and fallen feeds discharged into water caused by raising ducks to become a nutrient source of fish, frogs, plankton, algae, aquatic plants that are raised respectively in the water area. Thus, organisms and plants produced in the area can be recycled to become part of the alternative feeds for the ducks, thereby forming a virtuous cycle ecology of multiple raising, attaining economic benefits of full utilization of resources and the environmental control effect of reducing pests and diseases, and achieving a raising method that significantly improves the quality of ducks and their duck eggs.

The prior patent application can only solve the problem of duck feces and problems of supplying the fertilizer source for aquatic plants and feed source for aquatics. However, it cannot include industries such as agriculture and animal husbandry, and it is difficult to build a food chain. Meanwhile, it cannot combine with the consumer side to build a complete food supply chain.

There is also a Taiwan Utility Model No. M543545 "automatic monitoring system for multi-polyculture" issued on Jun. 21, 106th year of the Republic Era mainly includes a three-dimensional building, a planting section, a water treatment system, an environmental sensing system, an environmental control system and a main control system. The three-dimensional building has at least one floor. A poultry farming section can be set in each floor. The planting section can be set in each floor. The water treatment system can be disposed in each floor and has a fish pond, a first pump, an aeration tank, a multi-layer water filtering device, a pure water storage tank and a second pump. The environment sensing system can be disposed in each floor and has a gas sensing device, a light sensing device, a temperature sensing device, a humidity sensing device and a water quality sensing device. The environmental control system can be disposed in each floor and has a humidity control device, a ventilation control device, a light guiding device and a water quality adjusting device. The main control system can monitor the water treatment system, the environmental sensing system and the environmental control system.

Although the prior patent application solves the problems of poultry feeding, feces removal, aquatics feeding, regular water exchange, and house plants watering and sun exposure, it does not combine the production of animal husbandry and food processing, nor does it combine the disclosure of the consumer side. In addition, it cannot be made into food in an effective time to reach the consumer. Therefore, it cannot build a culturing system with complete food supply chain and waste environmental treatment.

The current consuming behavior has changed into electronic consumption mode. For example, the Taiwan Utility Model No. M547138 "shopping system" issued on Aug. 11, 106th year of the Republic Era discloses a shopping platform server for selling products and executing consumption after a merchant and a consumer connect to the server via information. It mainly allows the consumer to purchase discount points on the shopping platform and use the discount points to purchase products sold by the merchant or purchase at a brick-and-mortar store of the merchant. With a discount of the discount points, the consumer is allowed to receive discounts without restricting purchased products, thereby achieving an effect of diversified selection. The merchant can also achieve advertising benefits through the shopping platform server, thereby attracting a large number of people and saving costs.

Since the prior patent application attracts the consumer to purchase with promotional discounts, the purchased products are often not necessities for consumers, and the purchased products are not articles, foods or food products that fit in with the consumer's health. Not only money but also time is wasted.

Further, with the rise of public awareness of health, the importance of exercise for maintaining own health is increasingly emphasized. Therefore, the Taiwan Utility Model No. M527997 "the health management platform for sport/fitness club" issued on Sep. 1, 105th year of the Republic Era discloses to set a personal health management platform on an official website in order that the consumer can log in and record all sport equipment, frequencies, time and personal fitness status for free. Meanwhile, individual courses are all put on the Internet. Each coach can help the consumer with his health management through recording the practice and growth curve of the consumer on the platform and cooperating with growing photos and graphs at various stages during the lessen.

Although the prior patent application establishes the unique exercise records and physical condition information for each consumer, the exercise time of each consumer is limited, the number and the time of coaches for teaching are also not many. Therefore, it cannot aim at each consumer to execute long-term teaching and training. It also cannot advise and control diet of the consumer during non-exercise time. Hence, it is still not ideal for use.

SUMMARY OF THE INVENTION

Thus, the current production and consumption systems of various industries still includes the above disadvantages.

A production and consumption system of three-dimensional vertical planting landscape and capable of achieving healthy, low-cost and environmental protection of this invention is disclosed and comprises an aquatic raising zone for raising at least one aquatic animal, a crop planting zone connected to the aquatic raising zone for planting at least one crop, an animal raising zone connected to the crop planting zone for raising at least one edible animal, an insect culturing zone connected to the aquatic raising zone and the animal raising zone for providing a source of required feeds for the aquatic animal and the edible animal, a food processing zone connected to the aquatic raising zone, the crop planting zone and the animal raising zone and having a slaughtering area for slaughtering the aquatic animal and the edible animal to become meat, a cooking area for cooking the meat with the crop into food, a freezing area for processing the aquatic animal, the meat, the crop and the food into frozen food for preservation and a canning area for processing the food into canned food for long-term preservation, a consumption zone connected to the aquatic raising zone, the crop planting zone, the animal raising zone, the insect culturing zone and the food processing zone and having a shopping area for providing a variety of products for purchase, a beverage area for providing a variety of beverages for purchase, a fresh supermarket area for selling the aquatic animal, the crop, the meat, the frozen food and the canned food, a barbecue and camping area for providing barbecue and camping activities, a food area for selling the food and a consumption data subsystem, and a sport health zone having at least one bikeway, a three-dimensional sidewalk, a plurality of health testing stations and a health data subsystem. The bikeway and the three-dimensional sidewalk are connected to the aquatic raising zone, the crop planting zone, the animal raising zone, the insect culturing zone, the food processing zone and the consumption zone. The health testing stations are disposed in the three-dimensional sidewalk and provided with a plurality of artificial sport tracks. The artificial sport tracks have different rotational speeds and rotational directions for allowing a consumer to walk or run on the artificial sport tracks.

Preferably, an application is downloaded in a cell phone in order to connect with the consumption data subsystem and the health data subsystem through the application.

Preferably, the consumption data subsystem establishes and searches for a purchase traceability by scanning. The purchase traceability includes previous purchased date, product, amount and quantity. The consumption data subsystem proposes a shopping suggestion list based on the purchase traceability.

Preferably, purchased product is delivered to a designated place automatically, a parking area or an exit and payment is paid through the application after selecting product and quantity based on the shopping suggestion list and sending to the consumption data subsystem through the application.

Preferably, the consumption zone provides a storage area for placing personal belongings. The application is applied to set an opening password and calculate time and cost of the placement.

Preferably, the barbecue and camping area is further designed and planed a competition of survival in wild or extreme sports that is disposed with obstacle sport or extreme sport fields, different levels being provided according to different physical limits. The application is applied to broadcast a process of the competition and provide correct health concept, information, knowledge, remedy, first aid and prevention of various sport injuries.

Preferably, the rotational speeds and rotational directions of the artificial sport tracks are controlled automatically or manually.

Preferably, an elevating unit is applied to control any one side of two sides of the artificial sport tracks automatically or manually to allow the artificial sport tracks to have different elevation angles.

Preferably, the health testing stations have a plurality of various measuring devices for measuring a physiological data of heartbeat, blood oxygen concentration and blood pressure after wearing.

Preferably, the physiological data measured by the measuring devices is scored according to the physiological data and a general standard value or an achieving rate of a specific health target to give a health score. The physiological data and the health score are transmitted to the health data subsystem for recording and storing and compared with previous measured physiological data and health score after each measurement. The health data subsystem provides a sport suggestion list and a food suggestion list for reference.

Preferably, the health data subsystem is connected to a medical institution for providing the physiological data and the health score so that the medical institution can take the physiological data and the health score as reference during a treatment. The health data subsystem further provides an execution rate of the sport suggestion list and the food suggestion list or an achieving rate of the specific health target to the medical institution as reference for the treatment.

Preferably, a working transport lane is connected among the aquatic raising zone, the crop planting zone, the animal raising zone, the insect culturing zone, the food processing zone and the consumption zone.

Preferably, a motion path of the bikeway is designed with an elementary level, an intermediate level, an advanced level and a difficult level according to different difficulties for chosen. A motion path of the three-dimensional sidewalk is designed with an elementary level, an intermediate level, an advanced level and a difficult level according to different difficulties for chosen. A mixed motion path of the bikeway and the three-dimensional sidewalk is designed with an elementary level, an intermediate level, an advanced level and a difficult level according to different difficulties for chosen.

The advantages of this invention are described as follows:

1. Because the feed source of the aquatic animal, the fertilizer source in the crop planting zone, the feed source of the edible animal in the animal raising zone, the feed source of larvae in the insect culturing zone, and the source of ingredients in the food processing zone can be continuously obtained and supplied, and produced feces can be handled completely, it achieves the effect of entire self-sufficiency. No chemical fertilizer, somatorophic hormone, and antibiotic are required, thereby assisting in protecting the environment.

2. The produced aquatic animal, crop, meat and food can be quickly consumed by the consumer so that they can be eaten immediately while they are fresh, thereby greatly saving the time and costs of food inspection, production, transportation and storage.

3. Residual aquatic animal, crop, meat and food can be processed into frozen food for preservation or made into canned food for long-term preservation so as to avoid waste.

4. The consumption zone can attract a large number of consumers to increase consumption and income, while providing ecological education, amusement, shopping, sightseeing, eating, barbecue and camping activities to enhance the quality of life and life functions.

5. In particular, the bikeway, the elevated and greening three-dimensional sidewalk and artificial sport tracks of the sport health zone allow the consumer to go cycling, walking, running and other exercises to achieve functions of exercise and fitness and attain the effect of enjoying the scenery of the entire area.

6. Further, the artificial sport tracks can be automatically or manually controlled to have different rotational speeds and different rotational directions, and the elevating unit is applied to control any one side of the two sides of the artificial sport tracks automatically or manually so that the artificial sport tracks can be adjusted to have different elevation angles, thereby simulating the walking or running on uphill or downhill roads and performing different modes of exercises.

7. Moreover, it has a variety of measuring devices for the consumer to wear, thereby measuring the physiological data of heartbeat, blood oxygen concentration and blood pressure while the consumer is doing exercise in order to monitor the motion state of the consumer.

8. It combines consumption, exercise and health into one and allows the consumer to do exercise while shopping, thereby saving time greatly.

9. According to the consumer's purchase traceability, a shopping suggestion list can be automatically provided to the consumer's cell phone, thereby saving the time for selecting and meeting the purchasing requirements of the consumer.

10. The measured physiological data of the consumer is scored according to the general standard value or the achieving rate of a specific health target to give a health score, thereby allowing the consumer to know his health condition.

11. After assessing by the of health data subsystem, it provides a sport suggestion list and a food suggestion list for reference that fit the consumer to allow the consumer to do exercise and control diet and increase achievement and efficiency of exercise and fitness.

12. If the consumer does not do exercise and control diet according to the sport suggestion list and the food suggestion list, it provides the execution rate of the sport suggestion list and the food suggestion list and the achieving rate of the specific health target to a medical institution as reference for a treatment.

13. It is further possible to design a competition of survival in wild or extreme sports that is disposed with obstacle sport or extreme sport fields which have different levels according to different physical limits for the consumer to join the competition. The application is applied to broadcast the competition and provide correct health concept, information, knowledge, remedy, first aid and prevention of various sport injuries to the consumer.

DETAILED DESCRIPTION OF THE PREFERRED EMBODIMENTS

Figure 1:
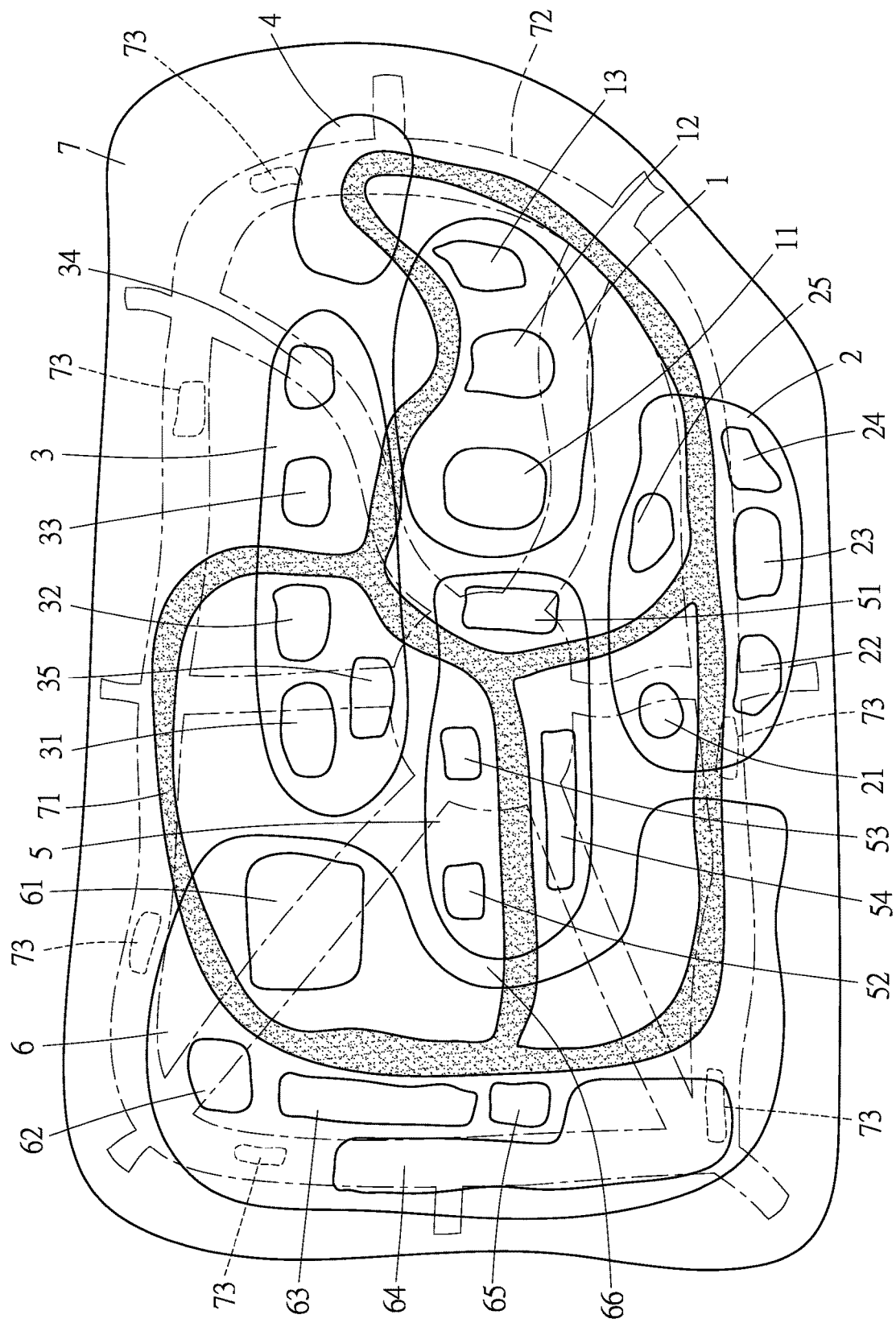
FIG. 1 is a schematic view showing related configuration of a preferred embodiment of this invention.
Figure 2:
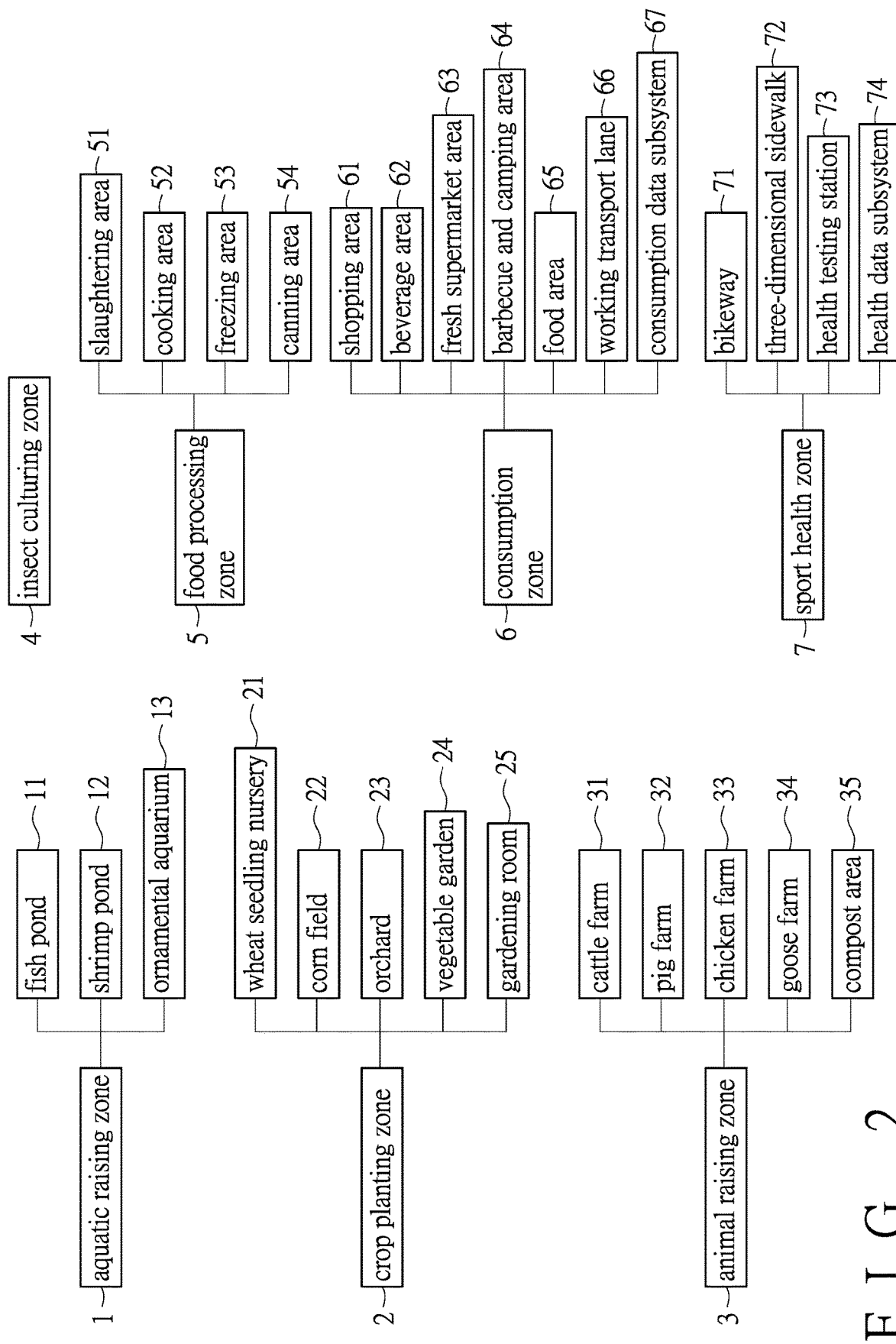
FIG. 2 is a block plan view of the preferred embodiment of this invention.
Figure 3:
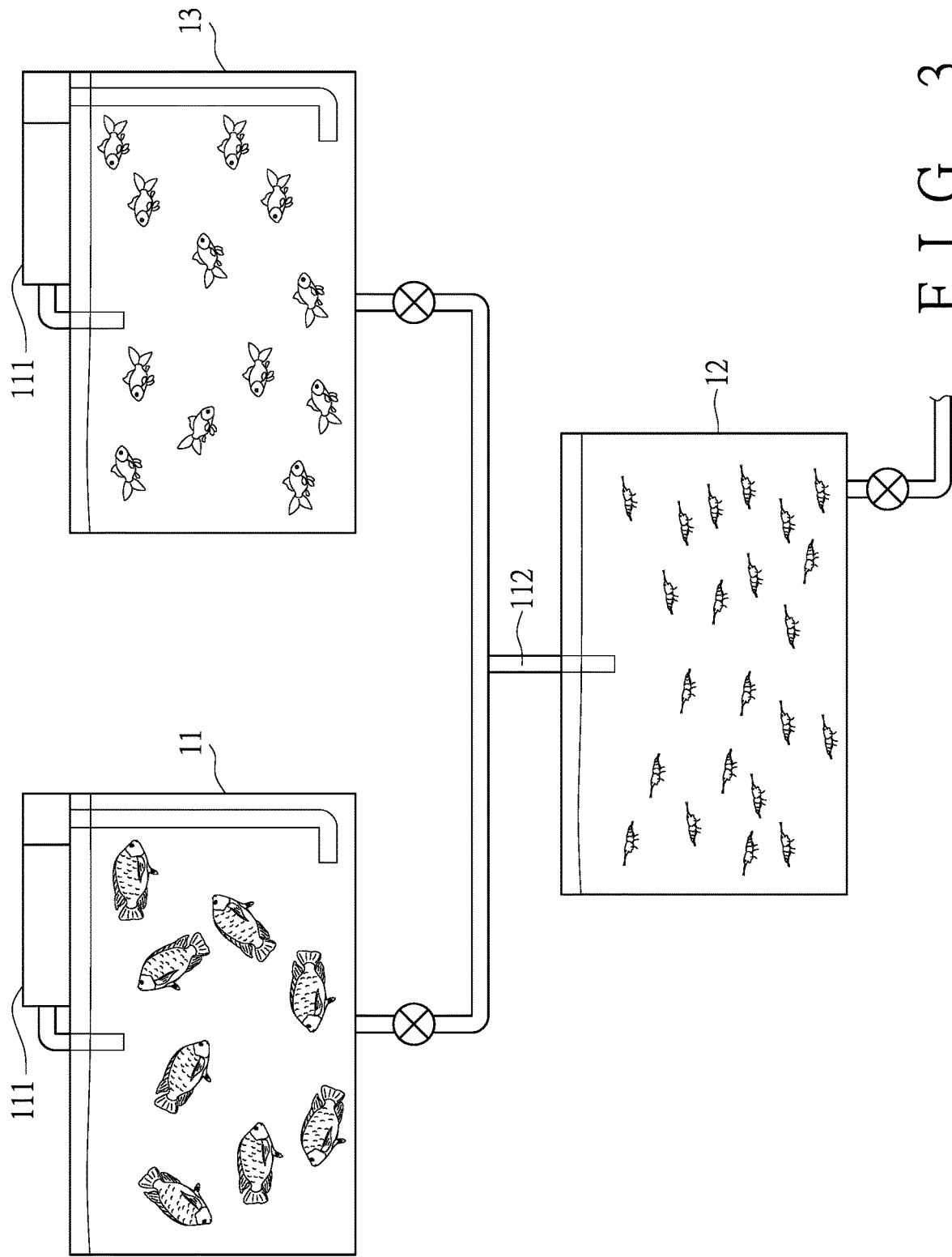
FIG. 3 is a schematic view showing a structure of a filter of the aquatic raising zone.

Referring to FIG. 1 and FIG. 2, a preferred embodiment of this invention is disclosed that comprises an aquatic raising zone 1, a crop planting zone 2, an animal raising zone 3, an insect culturing zone 4, a food processing zone 5, a consumption zone 6 and a sport health zone 7, wherein The aquatic raising zone 1 includes at least one fish pond 11, a shrimp pond 12 and an ornamental aquarium 13 for raising at least one aquatic animal. The fish pond 11 which is for raising an edible fish achieves a function of recreational fish fishing and allows a consumer to roast the fished fish while fishing. The shrimp pond 12 which is for raising an edible shrimp also achieves the function of recreational shrimp fishing and allows the consumer to roast the fished shrimp while fishing. The ornamental aquarium 13 is for raising an ornamental fish. The water for use in the fish pond 11 and the ornamental aquarium 13 is separately filtered through a filter 111, as shown in FIG. 3. The water filtered by the filter 111 then circulates to be delivered to the fish pond 11 and the ornamental aquarium 13 for continuous usage. Simultaneously, accumulated feces are separated from the fish pond 11 and the ornamental aquarium 13 and delivered to the shrimp pond 12 through a pipe 112 for use as feeds for the edible shrimp.

Figure 4:
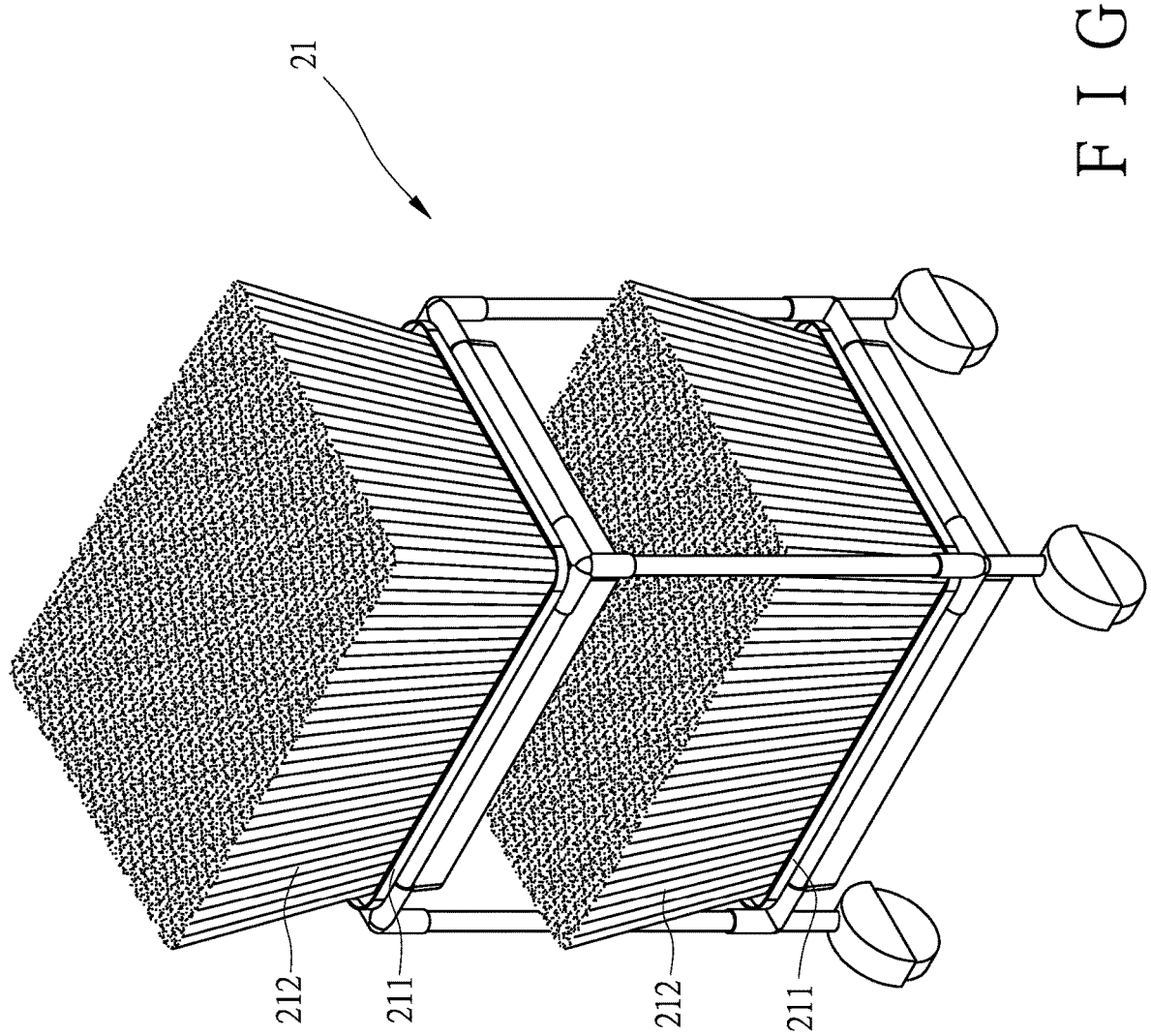
FIG. 4 is a schematic view showing one cultivation tray in the wheat seedling nursery is piled above another.

A crop planting zone 2 is connected to the aquatic raising zone 1 for growing at least one crop. The crop planting zone 2 includes at least one wheat seedling nursery 21, a corn field 22, an orchard 23, a vegetable garden 24 and a gardening room 25. The wheat seedlings nursery 21 is fixed through a plurality of cultivation trays 211 which are piled above each other, as shown in FIG. 4. A plurality of wheat seedlings 212 is planted in the cultivation trays 211 via hydroponics. The corn field 22 is for growing a corn. The orchard 23 is for planting a variety of fruits. The vegetable garden 24 is for growing a variety of vegetables. The gardening room 25 is for planting a variety of flowers and trees. The wheat seedling nursery 21, the corn field 22, the orchard 23, the vegetable garden 24 and the gardening room 25 are irrigated by the waste water caused after changing the water of the fish pond 11, the shrimp pond 12 and the ornamental aquarium 13.

An animal raising zone 3 is connected to the crop planting zone 2 for raising at least one edible animal. The animal raising zone 3 includes at least one cattle farm 31, a pig farm 32, a chicken farm 33, a goose farm 34 and a compost area 35. The cattle farm 31 is for raising an edible cattle. The pig farm 32 is for raising an edible pig. The chicken farm 33 is for raising an edible chicken. The goose farm 34 is for raising an edible goose. The wheat seedlings 212 produced in the wheat seedling nursery 21 and the corn produced in the corn field 22 can be used for food for consumers. Remained corn stalks are used for feeding the edible cattle, the edible pig, the edible chicken and the edible goose as the feed source of vegetable protein. Feces of the edible cattle, the edible pig, the edible chicken and the edible goose are collected in the compost area 35, and thence fermented to become compost. The compost is then used as fertilizer in the corn field 22, the orchard 23, the vegetable garden 24 and the gardening room 25 for planting.

An insect culturing zone 4 is connected to the aquatic raising zone 1 and the animal raising zone 3. The insect culturing zone 4 is for raising at least one larva of an insect which may be a black soldier fly. The compost can be used for the feed for the larva of the insect. The larva is then used in the fish pond 11, the shrimp pond 12, the ornamental aquarium 13, the chicken farm 33 and the goose farm 34 as the feed source of animal protein.

A food processing zone 5 is connected to the aquatic raising zone 1, the crop planting zone 2 and the animal raising zone 3. The food processing zone 5 includes a slaughtering area 51, a cooking area 52, a freezing area 53 and a canning area 54. The slaughtering area 51 is for slaughtering the edible fish, the edible shrimp, the edible cattle, the edible pig, the edible chicken and the edible goose into a meat. The cooking area 52 is for cooking the meat with the various vegetables produced by the vegetable garden 24 into a food. The freezing area 53 is for processing the meat, the vegetables and the fruits into a frozen food for preservation. The canning area 54 is for making the meat, the vegetables and the fruits into a canned food for long-term preservation.

A consumption zone 6 is connected to the aquatic raising zone 1, the crop planting zone 2, the animal raising zone 3, the insect culturing zone 4 and the food processing zone 5. The consumption zone 6 includes a shopping area 61, a beverage area 62, a fresh supermarket area 63, a barbecue and camping area 64 and a food area 65.

The shopping area 61 provides a variety of products for purchase. The beverage area 62 provides a variety of beverages for purchase. The fresh supermarket area 63 sells the frozen food or the canned food of the meat, the vegetables and the fruits. The barbecue and camping area 64 allows the consumer to have activities such as barbecue and camping. The food area 65 sells the cooked food. In addition, consumption caused by any of the above-mentioned activities can be done through mobile payment. A purchased product is delivered to the consumer's house directly via delivery service, thereby saving costs and time for delivery and increasing the convenience. Further, a working transport lane 66 is connected among the aquatic raising zone 1, the crop planting zone 2, the animal raising zone 3, the insect culturing zone 4, the food processing zone 5 and the consumption zone 6 whereby a worker can deliver the aquatic animal, the crop, the edible animal, the meat, the canned food and other commodities quickly through the working transport lane 66.

The consumption zone 6 can establish a consumption data subsystem 67. The consumer downloads an application in his cell phone so that the consumer can connect to the consumption data subsystem 67 through the application. Therefore, any consumption in the consumption zone 6 can be authenticated and identified through the application. When the consumer enters into the consumption zone 6, the consumption data subsystem 67 can establish and search for a previous purchase traceability of the consumer through scanning. The purchase traceability records a history of purchased date, product, amount and quantity about the consumer's previous consumption. A shopping suggestion list is provided to the consumer's cell phone as reference for purchasing based on the purchase traceability, and for calculating a budget, controlling the expense and providing promotion notices regularly. The consumer can select a preferred product and the quantity thereof through the cell phone. After the aforesaid information is transmitted to the consumption data subsystem 67 through the application, the purchased product is delivered to a place designated by the consumer automatically, or delivered to a parking area or an exit when the consumer is going to leave so that the consumer can take the purchased product away conveniently. Further, the payment is paid through the application. In addition, the purchased vegetables and fruits can be stored in a freezer in the fresh supermarket area 63. The consumer can retrieve the purchased vegetables and fruits when the consumer is going to leave. Moreover, the consumption zone 6 provides a storage area for placing personal belongings and the application is applied to set an opening password and calculate time and cost of the placement.

Figure 5:
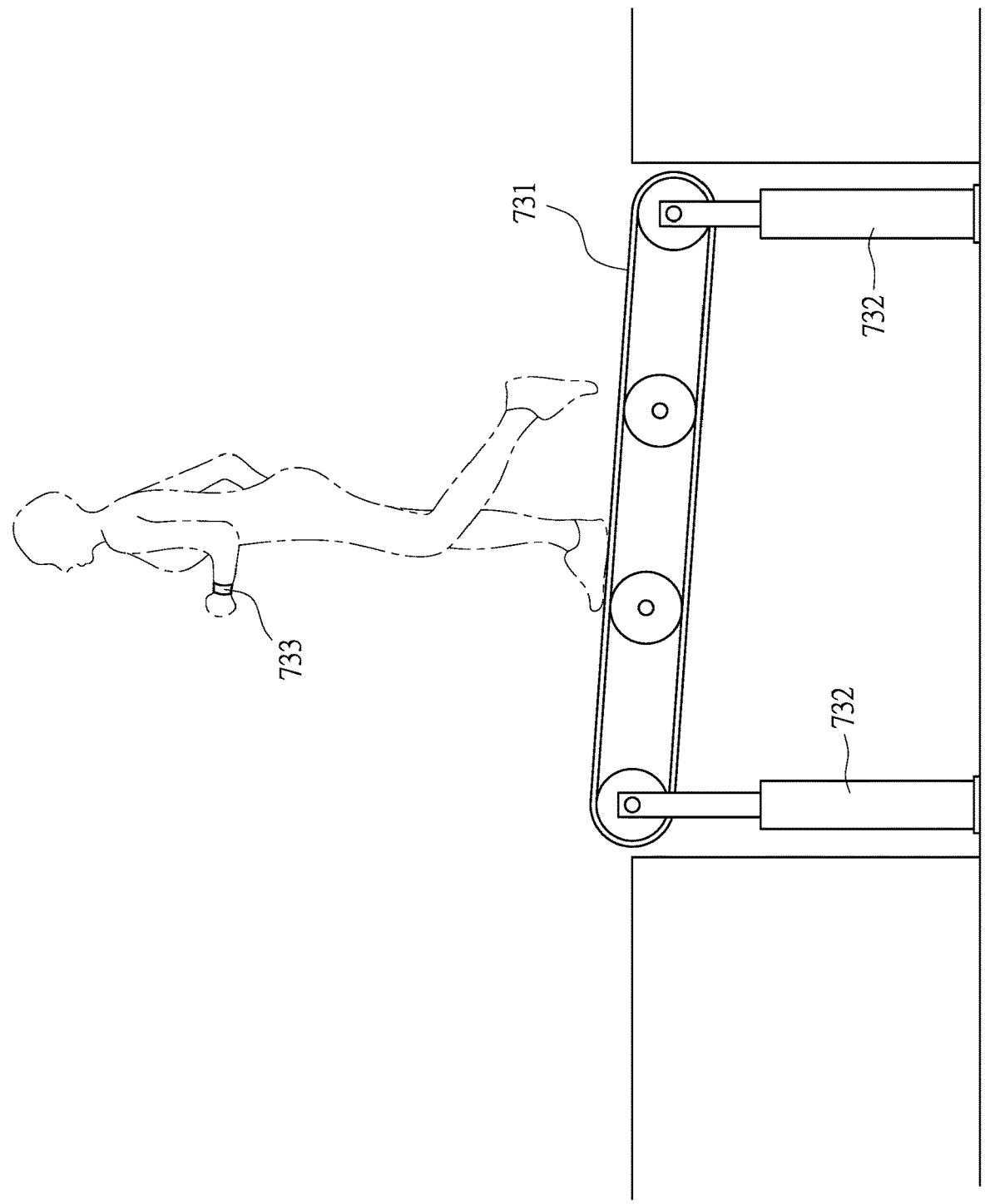
FIG. 5 is a schematic view showing the usage of the artificial sport tracks.
Figure 6:
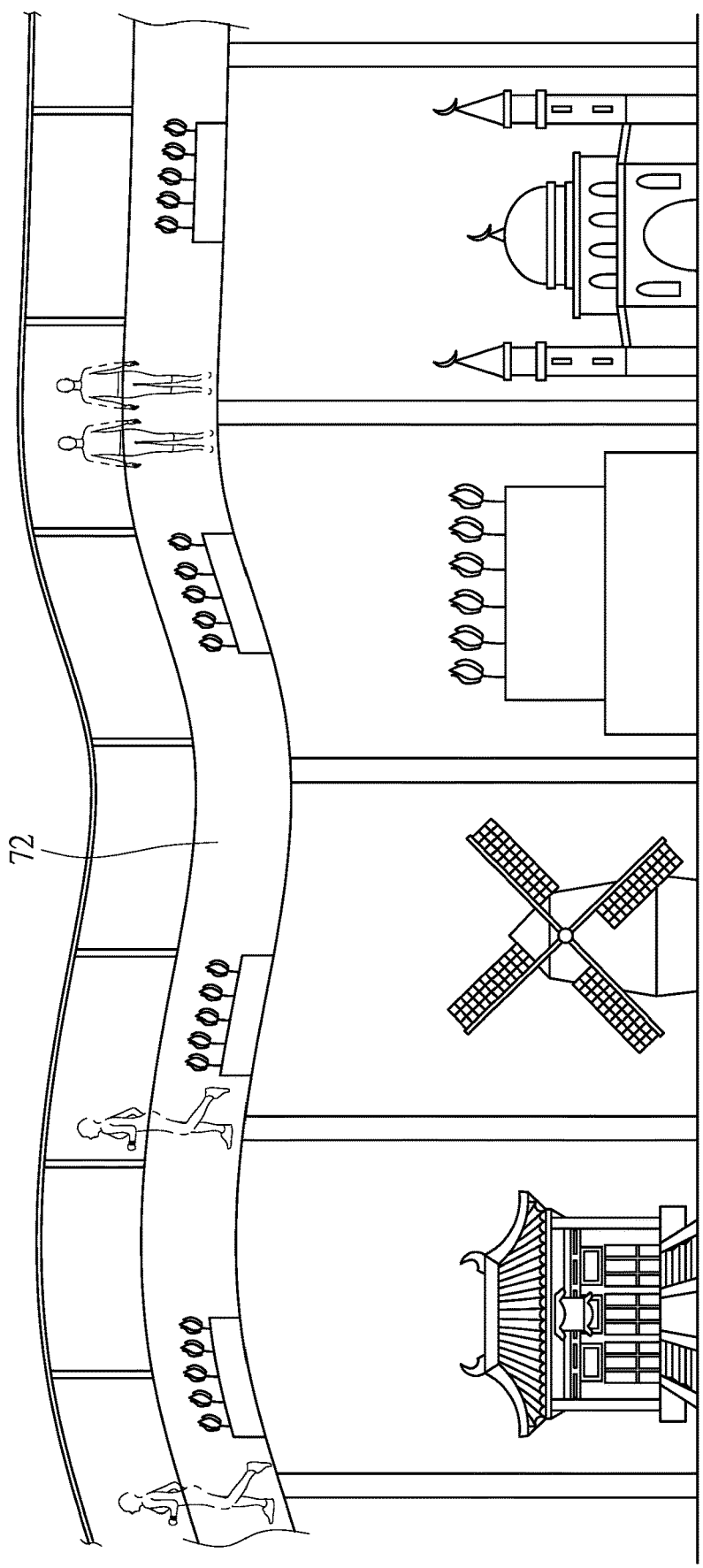
FIG. 6 is a schematic view showing the elevated three-dimensional sidewalk is arranged to be curved in different heights.

A sport health zone 7 includes at least one bikeway 71 on the ground, an elevated three-dimensional sidewalk 72 and a plurality of health testing stations 73. The sport health zone 7 is connected to the aquatic raising zone 1, the crop planting zone 2, the animal raising zone 3, the insect culturing zone 4, the food processing zone 5 and the consumption zone 6 through the bikeway 71 and the three-dimensional sidewalk 72 to allow the consumer to reach the aquatic raising zone 1, the crop planting zone 2, the animal raising zone 3, the insect culturing zone 4, the food processing zone 5 and the consumption zone 6 through bike riding for visits, ecological teaching, leisure, eating and consumption. Alternatively, the consumer can walk through the elevated three-dimensional sidewalk 72 which is arranged to be curved in different heights, as shown in FIG. 6 in order to enjoy the aquatic raising zone 1, the crop planting zone 2, the animal raising zone 3, the insect culturing zone 4, the food processing zone 5 and the consumption zone 6 from a commanding position to attain a beautiful landscape in different angles of vision. Meanwhile, Green plants which are arranged and planted at both sides of the three-dimensional sidewalk 72 can build a landscape of sky garden to increase the ornamental value. Moreover, the health testing stations can be disposed in the three-dimensional sidewalk 72. The health testing stations 73 are provided with a plurality of artificial sport tracks 731, as shown in FIG. 5. The artificial sport tracks 731 can be controlled to have different rotational speeds and rotational directions automatically or manually. The consumer needs to pass the authentication and identification through the application before walking or running on the artificial sport tracks 731. An elevating unit 732 is applied to control any one side of two sides of the artificial sport tracks 731 automatically or manually to allow the artificial sport tracks 731 to have different elevation angles in order to simulate the walking or running on uphill or downhill roads and allow the consumer to attain the effect of exercise and fitness. The health testing stations 73 have a variety of measuring devices 733 for measuring a physiological data of heartbeat, blood oxygen concentration and blood pressure while the consumer is doing exercise after wearing the measuring devices 733, thereby monitoring the motion state of the consumer. The sport health zone 7 is provided with a health data subsystem 74 in order to connect through the application. The health data subsystem 74 receives, records and stores each measured physiological data of heartbeat, blood oxygen concentration and blood pressure of the consumer and gives a health score according to the physiological data and a general standard value or an achieving rate of a specific health target. The health data subsystem 74 compares each measured physiological data and health score with the previous measured physiological data and health score after receiving in order to allow the consumer to know his health condition. After the consumer understands his health condition through the application, the health data subsystem 74 provides a sport suggestion list and a food suggestion list that are suitable for the consumer after executing the assessment based on the physiological data and the health score. The food suggestion list offers suggestions according to the consumer's nutritional needs of his body. The sport suggestion list includes various exercises. For example, a motion path of the bikeway 71 is designed with an elementary level, an intermediate level, an advanced level and a difficult level according to different difficulties for chosen. A motion path of the three-dimensional sidewalk 72 is also designed with an elementary level, an intermediate level, an advanced level and a difficult level according to different difficulties for chosen. Meanwhile, a mixed motion path of the bikeway 71 and the three-dimensional sidewalk 72 is designed with an elementary level, an intermediate level, an advanced level and a difficult level according to different difficulties for chosen. Before participating, the consumer has to pass the assessment executed by the health data subsystem 74. Therefore, the consumer can do exercise which is fit for his health condition based on the suggestions in the sport suggestion list. If the consumer feels unwell during doing the exercise, the worker can immediately handle, discontinue or afford first aid to ensure his safety. Meanwhile, the health data subsystem 74 is connected to a medical institution for providing the physiological data of heartbeat, blood oxygen concentration and blood pressure and the health score so that the medical institution can take the physiological data and the health score as reference during a treatment. The health data subsystem 74 further provides an execution rate of the sport suggestion list and the food suggestion list or the achieving rate of the specific health target to the medical institution as reference during the treatment when the consumer does exercise and controls diet without following the sport suggestion list and the food suggestion list. For example, if the consumer does not follow the suggestions in the sport suggestion list and does exercise every time, the absent times of the consumer will be recorded to calculate the achieving rate. Or, the consumer does not follow the recommended period of exercise time every time and reduces the exercise time upon himself, it calculates the execution rate. Further, if the consumer does not eat or purchase by following the recommended times and types in the food suggestion list, it calculates the achieving rate and execution rate and notifies the medical institution where the consumer visits through the application after a period of time.

Except providing the activities of barbecue and camping for the consumer, the barbecue and camping area 64 is further designed to invite the consumer to participate a competition of survival in wild or extreme sports which is planed based on professional health arrangement. It is provided with obstacle sport or extreme sport fields which have different levels according to different physical limits. For example, the levels can be divided into a level A, a level B, a level C, a level D and a difficult level. The challenging cycle can be divided into one day, three days, five days, ten days and fourteen days. In order to increase the consumer's interest and participation, prizes can be provided, such as trophies and rewards to encourage the consumer to challenge himself. If the consumer feels unwell during the competition, the worker can immediately handle, discontinue or afford first aid to ensure his safety. In addition, the application is applied to broadcast a process of the competition and a host of the competition can take the opportunity to educate all consumers to show and demonstrate how each invited contestant controls diet and does exercise correctly through the application. Meanwhile, via broadcasting the program through the application, the host can also instill a correct health concept, information and knowledge in the participating consumers, and can also announce, praise and reward the participating consumer who achieves the progressive improvement of physical and mental health. Further, through the live stream of the application, the host can also take the opportunity to educate the consumer about how to remedy, afford first aid and avoid various sport injuries.

Therefore, this invention combines consumption and exercise together, and allows the consumer to do exercise while shopping, thereby saving time. According to the purchase traceability of the consumer, the shopping suggestion list can be automatically sent to the consumer's cell phone, thereby saving the time for selecting and meeting the purchasing demands of the consumer. After the assessment executed by the health information subsystem 74, the sport suggestion list and the food suggestion list that are suitable for the consumer are sent to the consumer's cell phone, thereby allowing the consumer to do exercise and control diet while not doing exercise and increasing the achievement and efficiency of exercise and fitness.

Therefore, the preferred embodiment of this invention uses the edible fish and the edible shrimp produced in the fish pond 11 and the shrimp pond 12 of the aquatic raising zone 1 to become the ingredient cooked, frozen and canned in the food processing zone 5 for the consumer to eat or preserve. In addition, the feces of the edible fish and the ornamental fish can be used as feeds for the edible shrimp.

The waste water caused by changing water in the fish pond 11, the shrimp pond 12 and the ornamental aquarium 13 can be delivered to the wheat seedling nursery 21, the corn field 22, the orchard 23, the vegetable garden 24 and the gardening room 25 as irrigating water.

Part of the crops such as wheat seedlings or corn stalks produced in the crop planting zone 2 can be used for feeding the edible cattle, the edible pig, the edible chicken and the edible goose in the animal raising zone 3 as the feed source of vegetable protein. The feces of the edible cattle, the edible pig, the edible chicken and the edible goose are collected and fermented to become compost for use as fertilizer in the corn field 22, the orchard 23, the vegetable garden 24 and the gardening room 25. The raised edible cattle, the edible pig, the edible chicken and the edible goose are sent to the food processing zone 5 for slaughtering and processing into the meat, food, frozen food and canned food for the consumer to eat and purchase. Viscera and feathers of the slaughtered animal can be processed into fertilizer for composting and feeding the larva of the black soldier fly in the insect culturing zone 4. The larva is then used to feed the edible fish, the ornamental fish, the edible chicken and the edible goose as the feed source of animal protein.

Thus, both the feed source and the waste water in the aquatic raising zone 1 can be repeatedly filtered for reuse. The source of fertilizer in the crop planting zone 2, the feed source of animals, the treatment of the feces and other animal wastes in the animal raising zone 3, the feed source of the larva of the insect in the insect culturing zone 4, and the source of the ingredient in the food processing zone 5 can be continuously supplied and treated to achieve self-sufficiency entirely whereby no chemical fertilizer is required and the generation of wastes is reduced that assist in protecting the environment.

Moreover, the consumption zone 6 is applied to attract a large number of the consumers to increase consumption and income. Meanwhile, it can provide ecological education, amusement, shopping, sightseeing, eating, barbecue and camping activities to enhance the quality of life and life functions. The produced fish, shrimp, fruits, vegetables, meat and food can be quickly consumed through the prompt consumption of the consumer, thereby greatly saving the time and costs of food production, inspection, processing, transportation and storage.

Through the bikeway 71 and the elevated and greening three-dimensional sidewalk 72, the consumer can enjoy the different scenery of the entire area. The sport health zone 7 achieves the effects of exercise, fitness, and health monitoring while the consumer is shopping and sightseeing.

While the preferred embodiments of this invention are shown and described, the operation, use and effects of this invention are fully understood, however, the above-described embodiments are merely the preferred embodiments of this invention and that cannot restrict the scope of this invention. Further variations and modifications made based on the claims and the specification of this invention are included within the scope of this invention.

What is claimed is:

1. A production and consumption system of three-dimensional vertical planting landscape and capable of achieving healthy, low-cost and environmental protection comprising:

an aquatic raising zone raising at least one aquatic animal;

a crop planting zone connected to said aquatic raising zone for planting at least one crop;

an animal raising zone connected to said crop planting zone for raising at least one edible animal;

an insect culturing zone connected to said aquatic raising zone and said animal raising zone for providing a source of required feed for said at least one aquatic animal and said at least one edible animal;

a food processing zone connected to said aquatic raising zone, said crop planting zone and said animal raising zone, said food processing zone including a slaughtering area, a cooking area, a freezing area and a canning area, said slaughtering area being for slaughtering said aquatic animal and said edible animal to become meat, said cooking area being for cooking said meat with said crop into food, said freezing area being for processing said aquatic animal, said meat, said crop and said food into frozen food for preservation, said canning area being for processing said food into canned food for long-term preservation;

a consumption zone connected to said aquatic raising zone, said crop planting zone, said animal raising zone, said insect culturing zone and said food processing zone, said consumption zone including a shopping area, a beverage area, a fresh supermarket area, a barbecue and camping area, a food area and a consumption data subsystem, said shopping area providing a variety of products for purchase, said beverage area providing a variety of beverages for purchase, said fresh supermarket area selling said aquatic animal, said crop, said meat, said frozen food and said canned food, said barbecue and camping area providing barbecue and camping activities, and said food area selling said food; and a sport health zone including at least one bikeway, a three-dimensional sidewalk, a plurality of health testing stations and a health data subsystem, said bikeway and said three-dimensional sidewalk being connected to said aquatic raising zone, said crop planting zone, said animal raising zone, said insect culturing zone, said food processing zone and said consumption zone, said plurality of health testing stations being disposed in said three-dimensional sidewalk, said plurality of health testing stations being provided with a plurality of artificial sport tracks, said plurality of artificial sport tracks having different rotational speeds and rotational directions for allowing a consumer to walk or run on said artificial sport tracks;

wherein an application is downloaded in a cell phone in order to connect with said consumption data subsystem and said health data subsystem through said application; and said barbecue and camping area is further designed and planed a competition of survival in wild or extreme sports that is disposed with obstacle sport or extreme sport fields, different levels being provided according to different physical limits, said application being applied to broadcast a process of said competition and provide correct health concept, information, knowledge, remedy, first aid and prevention of various sport injuries.

2. The system as claimed in claim 1, wherein said consumption data subsystem establishes and searches for a purchase traceability by scanning, said purchase traceability including previous purchased date, product, amount and quantity, said consumption data subsystem proposing a shopping suggestion list based on said purchase traceability.

3. System as claimed in claim 2, wherein purchased product is delivered to a designated place automatically, a parking area or an exit and payment is paid through said application after selecting product and quantity based on said shopping suggestion list and sending to said consumption data subsystem through said application.

4. The system as claimed in claim 1, wherein said consumption zone provides a storage area for placing personal belongings, said application being applied to set an opening password and calculate time and cost of the placement.

5. The system as claimed in claim 1, wherein said rotational speeds and rotational directions of said plurality of artificial sport tracks are controlled automatically or manually.

6. The system as claimed in claim 1, wherein an elevating unit is applied to control any one side of two sides of said plurality of artificial sport tracks automatically or manually to allow said artificial sport tracks to have different elevation angles.

7. The system as claimed in claim 1, wherein said plurality of health testing stations has a plurality of various measuring devices for measuring a physiological data of heartbeat, blood oxygen concentration and blood pressure after wearing.

8. The system as claimed in claim 7, wherein said physiological data measured by said plurality of measuring devices is scored according to said physiological data and a general standard value or an achieving rate of a specific health target to give a health score, said physiological data and said health score being transmitted to said health data subsystem for recording and storing and compared with previous measured physiological data and health score after each measurement, said health data subsystem providing a sport suggestion list and a food suggestion list for reference.

9. The system as claimed in claim 8, wherein said health data subsystem is connected to a medical institution for providing said physiological data and said health score so that said medical institution can take said physiological data and said health score as reference during a treatment, said health data subsystem further providing an execution rate of said sport suggestion list and said food suggestion list or an achieving rate of said specific health target to said medical institution as reference for said treatment.

10. The system as claimed in claim 1, wherein a working transport lane is connected among said aquatic raising zone, said crop planting zone, said animal raising zone, said insect culturing zone, said food processing zone and said consumption zone.

11. The system as claimed in claim 1, wherein a motion path of said bikeway is designed with an elementary level, an intermediate level, an advanced level and a difficult level according to different difficulties for chosen, a motion path of said three-dimensional sidewalk being designed with an elementary level, an intermediate level, an advanced level and a difficult level according to different difficulties for chosen, a mixed motion path of said bikeway and said three-dimensional sidewalk being designed with an elementary level, an intermediate level, an advanced level and a difficult level according to different difficulties for chosen.

12. A production and consumption system of three-dimensional vertical planting landscape and capable of achieving healthy, low-cost and environmental protection comprising:
   an aquatic raising zone raising at least one aquatic animal;
   a crop planting zone connected to said aquatic raising zone for planting at least one crop;
   an animal raising zone connected to said crop planting zone for raising at least one edible animal;
   an insect culturing zone connected to said aquatic raising zone and said animal raising zone for providing a source of required feed for said at least one aquatic animal and said at least one edible animal;
   a food processing zone connected to said aquatic raising zone, said crop planting zone and said animal raising zone, said food processing zone including a slaughtering area, a cooking area, a freezing area and a canning area, said slaughtering area being for slaughtering said aquatic animal and said edible animal to become meat, said cooking area being for cooking said meat with said crop into food, said freezing area being for processing said aquatic animal, said meat, said crop and said food into frozen food for preservation, said canning area being for processing said food into canned food for long-term preservation;
   a consumption zone connected to said aquatic raising zone, said crop planting zone, said animal raising zone, said insect culturing zone and said food processing zone, said consumption zone including a shopping area, a beverage area, a fresh supermarket area, a barbecue and camping area, a food area and a consumption data subsystem, said shopping area providing a variety of products for purchase, said beverage area providing a variety of beverages for purchase, said fresh supermarket area selling said aquatic animal, said crop, said meat, said frozen food and said canned food, said barbecue and camping area providing barbecue and camping activities, and said food area selling said food; and
   a sport health zone including at least one bikeway, a three-dimensional sidewalk, a plurality of health testing stations and a health data subsystem, said bikeway and said three-dimensional sidewalk being connected to said aquatic raising zone, said crop planting zone, said animal raising zone, said insect culturing zone, said food processing zone and said consumption zone, said plurality of health testing stations being disposed in said three-dimensional sidewalk, said plurality of health testing stations being provided with a plurality of artificial sport tracks, said plurality of artificial sport tracks having different rotational speeds and rotational directions for allowing a consumer to walk or run on said artificial sport tracks;
   wherein said plurality of health testing stations has a plurality of various measuring devices for measuring a physiological data of heartbeat, blood oxygen concentration and blood pressure after wearing; and
   said physiological data measured by said plurality of measuring devices is scored according to said physiological data and a general standard value or an achieving rate of a specific health target to give a health score, said physiological data and said health score being transmitted to said health data subsystem for recording and storing and compared with previous measured physiological data and health score after each measurement, said health data subsystem providing a sport suggestion list and a food suggestion list for reference.

13. The system as claimed in claim 12, wherein said consumption data subsystem establishes and searches for a purchase traceability by scanning, said purchase traceability including previous purchased date, product, amount and quantity, said consumption data subsystem proposing a shopping suggestion list based on said purchase traceability.

14. System as claimed in claim 13, wherein purchased product is delivered to a designated place automatically, a parking area or an exit and payment is paid through said application after selecting product and quantity based on said shopping suggestion list and sending to said consumption data subsystem through said application.

15. The system as claimed in claim 12, wherein said consumption zone provides a storage area for placing personal belongings, said application being applied to set an opening password and calculate time and cost of the placement.

16. The system as claimed in claim 12, wherein said rotational speeds and rotational directions of said plurality of artificial sport tracks are controlled automatically or manually.

17. The system as claimed in claim 12, wherein an elevating unit is applied to control any one side of two sides of said plurality of artificial sport tracks automatically or manually to allow said artificial sport tracks to have different elevation angles.

18. The system as claimed in claim 12, wherein said health data subsystem is connected to a medical institution for providing said physiological data and said health score so that said medical institution can take said physiological data and said health score as reference during a treatment, said health data subsystem further providing an execution rate of said sport suggestion list and said food suggestion list or an achieving rate of said specific health target to said medical institution as reference for said treatment.

19. The system as claimed in claim 12, wherein a working transport lane is connected among said aquatic raising zone, said crop planting zone, said animal raising zone, said insect culturing zone, said food processing zone and said consumption zone.

20. The system as claimed in claim 12, wherein a motion path of said bikeway is designed with an elementary level, an intermediate level, an advanced level and a difficult level according to different difficulties for chosen, a motion path of said three-dimensional sidewalk being designed with an elementary level, an intermediate level, an advanced level and a difficult level according to different difficulties for chosen, a mixed motion path of said bikeway and said three-dimensional sidewalk being designed with an elementary level, an intermediate level, an advanced level and a difficult level according to different difficulties for chosen.

* * * * *